(12) United States Patent
Birnkrant et al.

(10) Patent No.: US 10,895,545 B2
(45) Date of Patent: Jan. 19, 2021

(54) METHOD OF DETECTING CONVERSION QUALITY OF GREEN MATRIX COMPOSITE MATERIAL AND SYSTEM FOR SAME

(71) Applicant: United Technologies Corporation, Farmington, CT (US)

(72) Inventors: Michael J. Birnkrant, Kenilworth, NJ (US); Wayde R. Schmidt, Pomfret Center, CT (US)

(73) Assignee: Raytheon Technologies Corporation, Farmington, CT (US)

( * ) Notice: Subject to any disclaimer, the term of this patent is extended or adjusted under 35 U.S.C. 154(b) by 1180 days.

(21) Appl. No.: 15/027,827

(22) PCT Filed: Sep. 26, 2014

(86) PCT No.: PCT/US2014/057621
§ 371 (c)(1),
(2) Date: Apr. 7, 2016

(87) PCT Pub. No.: WO2015/057370
PCT Pub. Date: Apr. 23, 2015

(65) Prior Publication Data
US 2016/0245767 A1     Aug. 25, 2016

Related U.S. Application Data

(60) Provisional application No. 61/890,775, filed on Oct. 14, 2013.

(51) Int. Cl.
*G01N 27/04*     (2006.01)
*F01D 25/00*     (2006.01)
(Continued)

(52) U.S. Cl.
CPC ............. *G01N 27/04* (2013.01); *F01D 5/282* (2013.01); *F01D 25/005* (2013.01); *G01N 21/66* (2013.01);
(Continued)

(58) Field of Classification Search
CPC .......... G01N 27/04; G01N 2021/8472; G01N 33/388; G01N 21/84; G01N 21/66;
(Continued)

(56) References Cited

U.S. PATENT DOCUMENTS

| 4,944,185 A | 7/1990 | Clark et al. |
| 5,240,329 A | 8/1993 | Zinkosky |

(Continued)

FOREIGN PATENT DOCUMENTS

| EP | 1679293 | 7/2006 |
| JP | H08254530 | 10/1996 |

OTHER PUBLICATIONS

The International Preliminary Report on Patentability for PCT Application No. PCT/US2014/057621, dated Apr. 28, 2016.
(Continued)

*Primary Examiner* — Melissa J Koval
*Assistant Examiner* — Trung Nguyen
(74) *Attorney, Agent, or Firm* — Carlson, Gaskey & Olds, P.C.

(57) ABSTRACT

A method of detecting conversion quality includes the steps of providing an article having a green material and a semiconductor material, processing the green material and the semiconductor material to produce a matrix composite, and detecting a matrix composite conversion quality with the semiconductor material.

21 Claims, 2 Drawing Sheets

(51) Int. Cl.
*G01N 21/84* (2006.01)
*G01N 33/38* (2006.01)
*F01D 5/28* (2006.01)
*G01N 21/66* (2006.01)

(52) U.S. Cl.
CPC .......... *G01N 21/84* (2013.01); *G01N 33/388* (2013.01); *F05D 2300/5023* (2013.01); *F05D 2300/6033* (2013.01); *G01N 2021/8472* (2013.01)

(58) Field of Classification Search
CPC ..... F05D 2300/6033; F05D 2300/5023; F01D 25/005; F01D 5/282
USPC ........ 324/693, 500, 600, 554, 663, 717, 719
See application file for complete search history.

(56) References Cited

U.S. PATENT DOCUMENTS

| | | | |
|---|---|---|---|
| 5,990,025 A * | 11/1999 | Suyama | ............... C04B 35/573 428/570 |
| 7,378,450 B2 | 5/2008 | Erkey et al. | |
| 7,451,657 B2 | 11/2008 | Goldfine et al. | |
| 7,855,449 B2 | 12/2010 | De Graff et al. | |
| 8,053,970 B2 | 11/2011 | Kimura et al. | |
| 8,378,668 B2 | 2/2013 | Faidi et al. | |
| 8,436,065 B2 | 5/2013 | Hwang et al. | |
| 8,442,301 B2 | 5/2013 | Dragovich et al. | |
| 2003/0129763 A1 | 7/2003 | Chambaerlain et al. | |
| 2005/0171703 A1 | 8/2005 | Goldfine et al. | |
| 2009/0014744 A1* | 1/2009 | Hsieh | ................... H01L 33/505 257/98 |
| 2010/0134098 A1 | 6/2010 | Faidi et al. | |
| 2010/0279845 A1* | 11/2010 | Kebbede | ............... C04B 35/573 501/90 |
| 2011/0053635 A1 | 3/2011 | Yang et al. | |
| 2011/0210658 A1 | 9/2011 | Pan et al. | |
| 2012/0202003 A1 | 8/2012 | McEnerney et al. | |
| 2013/0000861 A1 | 1/2013 | Hosek et al. | |
| 2014/0255665 A1* | 9/2014 | Hillier | ................... B32B 18/00 428/201 |

OTHER PUBLICATIONS

International Search Report and Written Opinion for PCT Application No. PCT/US2014/057621, dated Jan. 9, 2015.

Mentlik V et al, Examination of conversion degree of composite insulating materials, Electrical Insulation and Dielectric Phenomena, 2007. Ceidp 2007. Annual Report, Piscataway, NJ, Oct. 14, 2007, pp. 735-738.

The Partial European Search Report for EP Application No. 14854015.6, dated Jun. 23, 2017.

* cited by examiner

METHOD OF DETECTING CONVERSION QUALITY OF GREEN MATRIX COMPOSITE MATERIAL AND SYSTEM FOR SAME

CROSS-REFERENCE TO RELATED APPLICATIONS

This application claims priority to U.S. Provisional Application No. 61/890,775, which was filed on Oct. 14, 2013 and is incorporated herein by reference.

BACKGROUND

This disclosure relates to a matrix composite component, such as ceramic matrix composite (CMC) or organic matrix composite (OMC), and a method of detecting conversion quality of the green matrix composite material.

Gas turbine engines may be made more efficient, in part, by increasing engine operating temperatures. Exotic metallic components within the engine are already near their maximum operating temperatures. To further increase temperatures within the engine, CMC components are increasingly used and have higher temperature capabilities than more conventional materials.

One method of forming a CMC article includes providing a ceramic polymer precursor arranged in an article shape. The ceramic precursor is pyrolyzed to produce a CMC component having carbon or ceramic fibers interlinked with ceramic in a matrix. The CMC component is generally quite porous such that additional ceramic precursor is dispersed within the component and pyrolyzed additional times to increase the density to a sufficient level.

It is desirable to ensure that the ceramic precursor and carbon or ceramic fiber are sufficiently converted to a ceramic matrix composite material in order to provide desired density and strength to the finished component.

SUMMARY

In one exemplary embodiment, a method of detecting conversion quality includes the steps of providing an article having a green material and a semiconductor material, processing the green material and the semiconductor material to produce a matrix composite, and detecting a matrix composite conversion quality with the semiconductor material.

In a further embodiment of the above, the green material is a ceramic polymer precursor material. The processing step includes processing the ceramic polymer precursor material with the semiconductor material to produce a ceramic matrix composite. The detecting step includes detecting ceramic matrix composite conversion quality with the semiconductor material.

In a further embodiment of any of the above, the providing step includes wrapping ceramic polymer resin-embedded carbon or ceramic fibers about a form to provide the ceramic polymer precursor material.

In a further embodiment of any of the above, the ceramic polymer resin is a precursor to at least one of SiC, SiCN and SiN.

In a further embodiment of any of the above, the providing step includes integrating the semiconductor material into the ceramic polymer resin-embedded carbon or ceramic fibers.

In a further embodiment of any of the above, the semiconductor material includes at least one of Si, SiC, SiCN and SiN.

In a further embodiment of any of the above, the semiconductor material includes a structure that has a high surface area to volume ratio.

In a further embodiment of any of the above, the semiconductor material is an aerogel having submicron features.

In a further embodiment of any of the above, the processing step includes pyrolyzing the ceramic polymer resin-embedded carbon fibers and the semiconductor material.

In a further embodiment of any of the above, the article is impregnated with ceramic polymer resin and pyrolyzed multiple times to produce a ceramic matrix composite component.

In a further embodiment of any of the above, the detecting step includes applying a voltage to the semiconductor material to obtain a response from the semiconductor material indicative of a matrix composite conversion quality.

In a further embodiment of any of the above, the response is a light emission.

In a further embodiment of any of the above, the light emission includes a wavelength indicative of a desired ceramic matrix composite conversion quality.

In a further embodiment of any of the above, the response is a change in conductivity.

In a further embodiment of any of the above, the conductivity reaches a threshold indicative of a desired matrix composite conversion quality.

In a further embodiment of any of the above, the semiconductor material has a desired composition and crystallinity that is configured to produce the response which is indicative of a desired matrix composite conversion quality.

In a further embodiment of any of the above, the method of detecting conversion quality includes the steps of producing a matrix composite component that is one of a nacelle, engine component vane, blade, blade outer air seal, combustor liner or exhaust liner.

In a further embodiment of any of the above, the green material includes a monomer. The processing step includes processing the monomers into a polymer together with the semiconductor material to produce an organic matrix composite. The detecting step includes detecting an organic matrix composite quality with the semiconductor material.

In a further embodiment of the above, the providing step includes wrapping monomer-embedded carbon or ceramic fibers about a form to provide a component shape.

In a further embodiment of any of the above, the providing step includes integrating the semiconductor material into the monomer-embedded carbon or ceramic fibers.

In another exemplary embodiment, a gas turbine engine component includes a matrix composite material and a semiconductor material that is significantly less dense than the matrix composite material.

In a further embodiment of the above, the gas turbine engine component is one of a nacelle, engine component vane, blade, blade outer air seal, combustor liner or exhaust liner. The matrix composite material and the semiconductor material are provided by at least one of Si, SiC, SiCN and SiN.

BRIEF DESCRIPTION OF THE DRAWINGS

The disclosure can be further understood by reference to the following detailed description when considered in connection with the accompanying drawings wherein.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

DETAILED DESCRIPTION

Figure 1:
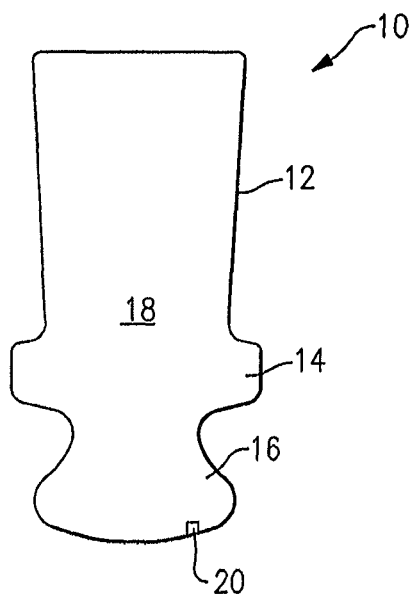
FIG. 1 is a schematic view of a ceramic matrix composite (CMC) component having a semiconductor material.

A matrix composite, such as an organic matrix composite (OMC) or ceramic matrix composite (CMC) component is schematically shown at 10 in FIG. 1. Although a CMC component is referenced throughout this disclosure, the disclosed method and apparatus also applies to OMC components. In the example, the CMC component is a turbine blade. However, it should be understood that the CMC component may be any structure, for example, a gas turbine engine blade, vane, blade outer air seal, combustor liner or exhaust liner.

The turbine blade 10 includes an airfoil 12 extending from a platform 14 that is supported by a root 16. The turbine blade 10 includes a green material, such as a ceramic polymer precursor material 18, which provides one or more of the airfoil 12, platform 14 and root 16. A semiconductor material 20 is integrated into the ceramic polymer precursor material 18 into a structural and/or non-structural portion of the CMC component. It may be desirable to integrate the semiconductor material 20 into a non-structural area of the turbine blade 10, for example, the bottom of the root 16.

In one example of the integrated semiconductor material 20, the ceramic polymer precursor is a silicon-based material, for example, Si, SiC, SiCN or SIN. This mixture forms the matrix in which fiber reinforcements are dispersed. These fibers may be composed of carbon, SiC or ceramic fibers. The semiconductor material is different than the ceramic precursor material, but is compatible with the ceramic polymer precursor such that the ceramic polymer precursor and semiconductor materials are integrated with one another in the finished CMC component.

The form of the semiconductor material that is integrated into the aerospace component may be a sheet, fiber or foam material. A desired characteristic is that one of the dimensions such as thickness, diameter, pore size or ligament circumference is less than 1 micron (0.000039 in).

In one example, a low density foam called an aerogel composed of silicon and/or carbon contains ligament and pore sizes that are less than 1 micron (0.000039 in). An aerogel is part of a class of materials known as nanocellular materials that have random, aperiodic or periodic pores and ligaments with dimensions that are less than a micron. The nanocellular semiconductor aerogel has a large surface area to volume ratio, which enables microscopic contact with the ceramic polymer precursor material.

Figure 2:
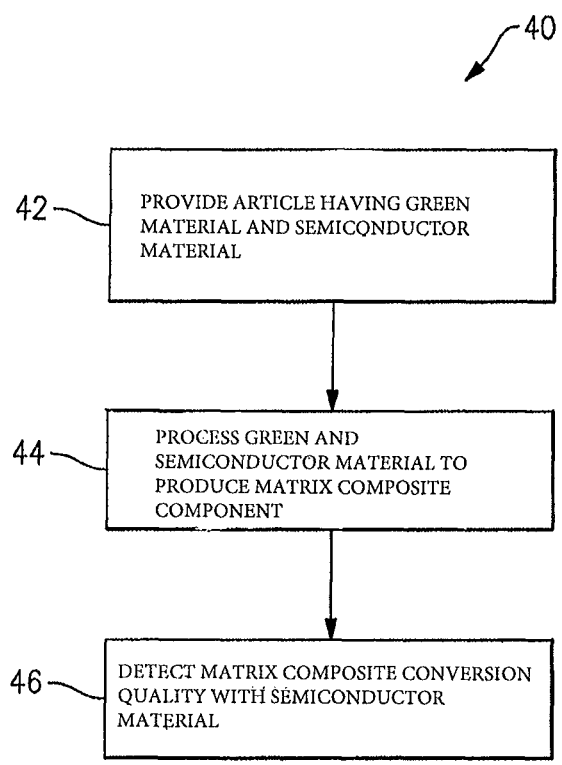
FIG. 2 is a flow chart depicting an example method of detecting matrix composite conversion quality.

An article is provided as indicated at 42 in the method 40 of FIG. 2. In one example, carbon or silicon-containing fibers are coated with a ceramic polymer precursor resin to provide a layer. Multiple layers are stacked into plies, and the plies are arranged about a form in the shape of an article. During article forming, the semiconductor material is integrated into the article to provide a semiconductor material. The ceramic polymer precursor and semiconductor material are processed to produce the CMC component, as indicated at block 44. In one example, the article is impregnated with additional ceramic polymer precursor, and the article is pyrolyzed multiple times to increase density. During processing, the conversion of ceramic polymer precursor to CMC is detected using the semiconductor material, as indicated at block 46.

Figure 3:
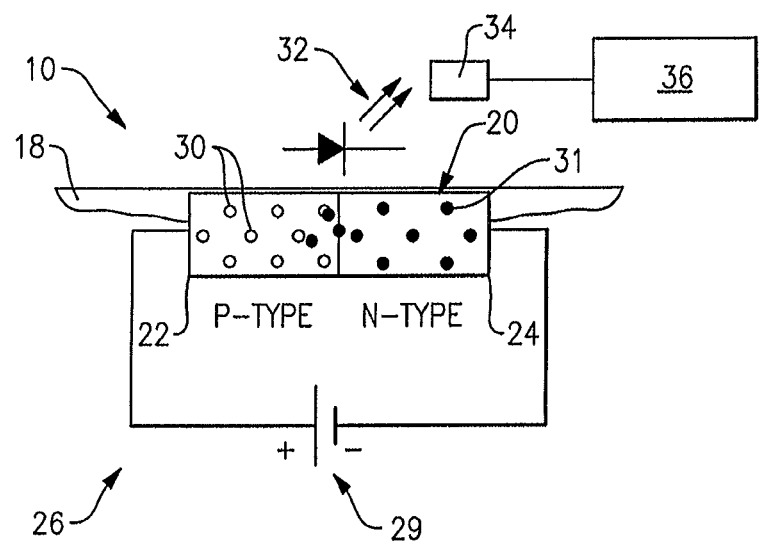
FIG. 3 is a schematic view of one example system for detecting matrix composite conversion quality.
Figure 4:
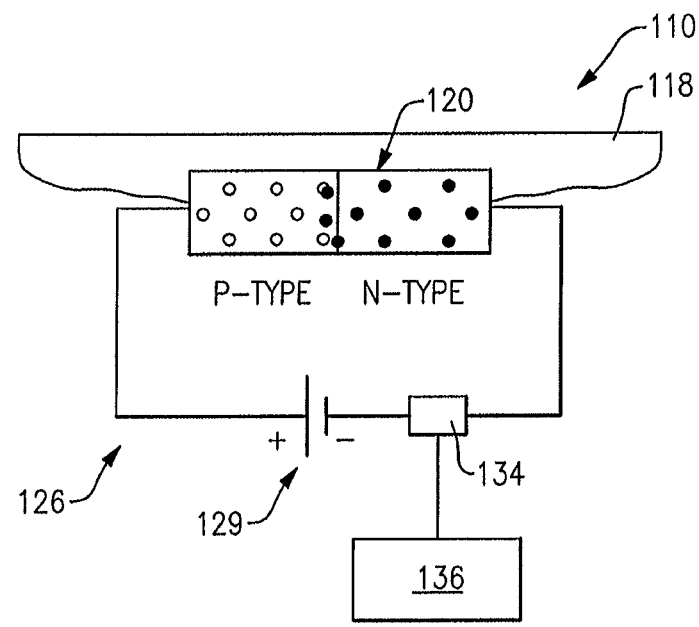
FIG. 4 is a schematic view of another example system for detecting matrix composite conversion quality.

Two example systems for detecting CMC conversion quality are shown in FIGS. 3 and 4. The principle of operation is based upon the semiconductor material, as shown in FIG. 3. As in other diodes, a p-n junction is established, current flows from the p-side (anode) 22, to the n-side (cathode) 24, of the semiconductor material 20 but not in the reverse direction. Charge carriers, electrons 31 and holes 30 flow into the junction from the electrodes with different voltages in response to the applied voltage 29 to a circuit 26, for example, about 1200 volts. When an electron 31 meets a hole 30, it falls into a lower energy level, and releases energy in the form of a photon. The wavelength of the light 32 emitted and, thus, its wavelength, depends on the band gap energy of the materials forming the p-n junction. The light 32 emitted is sensitive to doping elements that change the band gap energy. The semiconductor material can be doped by changing the chemical composition of the interface between semiconductor and the environment when the article has a large surface area to volume ratio. Thus, the band gap is sensitive to the environment, which influences the wavelength of light emitted in the semiconductor material 20.

During pyrolyzation of the ceramic polymer precursor material 18 and the semiconductor material 20, the silicon or carbon containing fibers and pre-ceramic interlink with one another to form a ceramic composite matrix. The semiconductor material 20 is exposed relative to the ceramic polymer precursor material 18. The conversion process alters the properties of the semiconductor material 20, which changes the light's wavelength emitted and, thus, can indicate the conversion of pre-ceramic to ceramic in manufacturing of the CMC component. As a result, a light sensor 34 in communication with a processor 36 detects the light 32, which corresponds to the properties of the semiconductor material 20 and the conversion from pre-ceramic to ceramic. In the example, once the sensor 34 detects a light has been given off indicative of a desired level of CMC conversion, the processor 36 will give an indication (for example, on a monitor) that a CMC component of sufficient quality has been manufactured.

In another example illustrated in FIG. 4, the semiconductor material 120 need not monitor the light emitted from the ceramic precursor material 118. The applied voltage 129 charges the semiconductor 120. The semiconductor 120 will change conductivity as the CMC conversion quality increases. A sensor 134 in the circuit 126 is monitored to detect a change in conductivity or resistance in the circuit from the change in the semiconductor 120 during the conversion process, which will be detected by the processor 136.

The composition and/or crystallinity of the semiconductor material may be modified to obtain a desired light wavelength or conductivity of the semiconductor 120 that corresponds to a desired level of CMC conversion quality. Thus, the semiconductor 120 may be tuned to provide a component quality threshold, such that a particular emitted light or detected conductivity corresponds to sufficient CMC conversion quality.

In another example, the disclosed semiconductor can be incorporated into an organic matrix composite (OMC) in order to monitor the quality of the component. In this case, the semiconductor device can be pre-fabricated and inserted into the OMC layup during preparation. The OMC is prepared by laying up plies in a mold and then infiltrated with monomers, which provides the green material. The monomers react to form a polymer. The physical properties of the OMC rely on the quality of the monomer conversion to polymer. The OMC quality monitoring is achieved using the same underlying principle in which the environment will influence the light emission from the semiconductor material. The semiconductor material is sensitive to the conversion of monomers to polymers and thus changes the wavelength of light emitted. The conversion of monomers to a polymer impact the performance of the component and thus monitoring the conversion quality is desired. Following the OMC processing steps to evaluate conversion quality can be achieved using the same method outline in FIG. 2. The OMC quality can be monitored via emission of light outlined in FIG. 3 or by monitoring changes in conductivity.

It should also be understood that although a particular component arrangement is disclosed in the illustrated embodiment, other arrangements will benefit herefrom. Although particular step sequences are shown, described, and claimed, it should be understood that steps may be performed in any order, separated or combined unless otherwise indicated and will still benefit from the present invention.

Although the different examples have specific components shown in the illustrations, embodiments of this invention are not limited to those particular combinations. It is possible to use some of the components or features from one of the examples in combination with features or components from another one of the examples.

Although an example embodiment has been disclosed, a worker of ordinary skill in this art would recognize that certain modifications would come within the scope of the claims. For that reason, the following claims should be studied to determine their true scope and content.

What is claimed is:

1. A method of detecting conversion quality, comprising the steps of:
    providing an article having a green material and a semiconductor material;
    integrating the semiconductor material into the green material to produce a matrix composite;
    detecting a matrix composite conversion quality with the semiconductor material, the detecting step includes applying a voltage to the semiconductor material to obtain a response from the semiconductor material indicative of a matrix composite conversion quality; and
    producing a matrix composite component if a sufficient matrix composite conversion quality is detected.

2. The method according to claim 1, wherein the green material is a ceramic polymer precursor material, the integrating step includes processing the ceramic polymer precursor material with the semiconductor material to produce a ceramic matrix composite, the detecting step includes detecting ceramic matrix composite conversion quality with the semiconductor material.

3. The method according to claim 2, wherein the providing step includes wrapping ceramic polymer resin-embedded carbon or ceramic fibers about a form to provide the ceramic polymer precursor material.

4. The method according to claim 3, wherein the ceramic polymer resin is a precursor to at least one of SiC, SiCN and SiN.

5. The method according to claim 3, wherein the providing step includes integrating the semiconductor material into the ceramic polymer resin-embedded carbon or ceramic fibers.

6. The method according to claim 5, wherein the semiconductor material includes at least one of Si, SiC, SiCN and SiN.

7. The method according to claim 6, wherein the semiconductor material includes a structure having a high surface area to volume ratio.

8. The method according to claim 6, wherein the semiconductor material is an aerogel having submicron features.

9. The method according to claim 5, wherein the integrating step includes pyrolyzing the ceramic polymer resin-embedded carbon fibers and the semiconductor material.

10. The method according to claim 9, wherein the article is impregnated with ceramic polymer resin and pyrolyzed multiple times to produce a ceramic matrix composite component.

11. The method according to claim 1, wherein the response is a light emission.

12. The method according to claim 11, wherein the light emission includes a wavelength indicative of a desired ceramic matrix composite conversion quality.

13. The method according to claim 1, wherein the response is a change in conductivity.

14. The method according to claim 13, wherein the conductivity reaches a threshold indicative of a desired matrix composite conversion quality.

15. The method according to claim 1, wherein the semiconductor material has a desired composition and crystallinity configured to produce the response which is indicative of a desired matrix composite conversion quality.

16. The method according to claim 1, wherein the matrix composite component is one of a nacelle, engine component vane, blade, blade outer air seal, combustor liner or exhaust liner.

17. The method according to claim 1, wherein the green material includes a monomer, the integrating step includes processing the monomers into a polymer together with the semiconductor material to produce an organic matrix composite, and the detecting step includes detecting an organic matrix composite quality with the semiconductor material.

18. The method according to claim 17, wherein the providing step includes wrapping monomer-embedded carbon or ceramic fibers about a form to provide a component shape.

19. The method according to claim 18, wherein the providing step includes integrating the semiconductor material into the monomer-embedded carbon or ceramic fibers.

20. A gas turbine engine component comprising:
    a matrix composite material and a semiconductor material that is significantly less dense than the matrix composite material, the semiconductor material has a submicron thickness, diameter, pore size or ligament circumference, the semiconductor material includes a p-n junction;
    wherein the semiconductor material is configured to provide a response to a voltage across the p-n junction that includes at least one of light emission and a conductivity, the response indicative of a matrix composite conversion quality.

21. The gas turbine engine component according to claim 20, wherein the gas turbine engine component is one of a nacelle, engine component vane, blade, blade outer air seal, combustor liner or exhaust liner, and the matrix composite material and the semiconductor material are provided by at least one of Si, SiC, SiCN and SiN.

\* \* \* \* \*